United States Patent [19]

Yoneyoshi et al.

[11] Patent Number: 4,760,149

[45] Date of Patent: Jul. 26, 1988

[54] ASYMMETRICALLY MODIFIED BORON HYDRIDE TYPE COMPOUND, A PRODUCTION METHOD THEREOF, AND A METHOD FOR PRODUCING AN OPTICALLY ACTIVE ALCOHOL DERIVATIVE BY THE USE THEREOF

[75] Inventors: Yukio Yoneyoshi, Ohtsu; Gohfu Suzukamo, Ibaraki; Kazuhiko Hamada, Kyoto; Toshio Nishioka, Ashiya, all of Japan

[73] Assignee: Sumitomo Chemical Company, Limited, Osaka, Japan

[21] Appl. No.: 781,453

[22] Filed: Sep. 30, 1985

Related U.S. Application Data

[63] Continuation-in-part of Ser. No. 688,287, Jan. 7, 1985, abandoned, which is a continuation-in-part of Ser. No. 674,924, Nov. 21, 1984, abandoned.

[30] Foreign Application Priority Data

Dec. 12, 1983 [JP] Japan .................................. 58-234859
Feb. 20, 1984 [JP] Japan .................................. 59-31127

[51] Int. Cl.$^4$ .......................................... C07D 249/08
[52] U.S. Cl. .................................... 548/262; 548/341; 564/8; 564/9
[58] Field of Search .................. 548/262, 341; 564/9, 564/8

[56] References Cited

U.S. PATENT DOCUMENTS 4,435,203 3/1984 Funaki et al. ...................... 548/262
4,554,007 11/1985 Funaki et al. ...................... 71/76

FOREIGN PATENT DOCUMENTS 0035355 9/1981 European Pat. Off. .

OTHER PUBLICATIONS

Borch, JOC 37 (1972) 2347.
Itsuno et al. I, JCS Chem. Comm. (1983) 469.
Itsuno et al II, "Asymmetric Synthesis, etc" 1983 CA 100:22184y 1983.
Itsuno et al. III, "Asymmetric Reduction, etc" 1984 CA 100:67806u 1984.
J. Chem. Soc. Perkin I, 1981, pp. 231–235, London, GB; M. F. Grundon et al. "Asymmetric Induction. Part 3. 1,2 Asymmetric Reduction of Ketones . . . ".

Primary Examiner—Glennon H. Hollrah
Assistant Examiner—P. L. Morris
Attorney, Agent, or Firm—Stevens, Davis, Miller & Mosher

[57] ABSTRACT

The present invention relates to an asymmetrically modified borohydride type compound obtained by reacting an optically active amino alcohol represented by the formula,

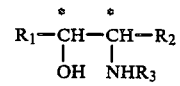

or its salt with an acid with a borohydride compound; its production method; and a method for producing an optically active alcohol derivative useful as fungicides, herbicides or plant growth regulators and represented by the formula,

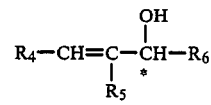

which comprises asymmetrically reducing a ketone compound represented by the formula,

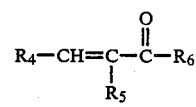

with the asymmetrically modified borohydride type compound.

23 Claims, No Drawings

ASYMMETRICALLY MODIFIED BORON HYDRIDE TYPE COMPOUND, A PRODUCTION METHOD THEREOF, AND A METHOD FOR PRODUCING AN OPTICALLY ACTIVE ALCOHOL DERIVATIVE BY THE USE THEREOF

CROSS-REFERENCE TO RELATED APPLICATIONS

The present application is a continuation-in-part application of application Ser. No. 688,287 filed Jan. 7, 1985, and now abandon. which is in turn a continuation-in-part application of application Ser. No. 674,924 filed Nov. 21, 1984 now abandoned.

TECHNICAL FIELD

The present invention relates to a novel asymmetrically modified boron hydride type compound, its production and a method for producing an optically active alcohol derivative using the compound. More particularly, it relates to an asymmetrically modified boron hydride type compound obtained by reacting an optically active amino alcohol represented by the formula (I),

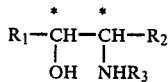

wherein $R_1$ represents an aryl, alkyl, cycloalkyl or aralkyl group, $R_2$ represents an aryl, alkyl, aralkyl or alkoxycarbonyl group, $R_3$ represents a hydrogen atom or an alkyl or aralkyl group, and a mark * means an asymmetric carbon, or its salt with an acid, with a boron hydride compound; its production method; and a method for producing an optically active alcohol derivative represented by the formula (III),

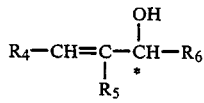

wherein $R_4$ represents an alkyl, cycloalkyl or cycloalkenyl group, or a phenyl group which may be substituted with a halogen atom or an alkyl, haloalkyl, cyano, alkoxyl, phenoxy or phenyl group, $R_5$ represents an imidazol-1-yl or 1,2,4-triazol-1-yl group, $R_6$ represents a tert-butyl group, or a 1,1-dimethyl-2-phenylethyl group wherein benzene ring may be substituted with a halogen atom, and a mark * has the same meaning as above, by carrying out the asymmetric reduction of a ketone compound represented by the formula (II),

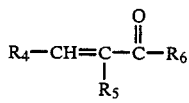

wherein $R_4$, $R_5$ and $R_6$ have the same meanings as above, with said asymmetrically modified boron hydride type compound.

BACKGROUND ART

The alcohol derivative represented by the above formula (III), i.e. an azole type $\alpha,\beta$-unsaturated alcohol derivative is known to be useful as an active ingredient for fungicides, plant growth regulators or herbicides, as represented for example by 1-(2,4-dichlorophenyl)-2-(1,2,4-triazol-1-yl)-4,4-dimethyl-1-penten-3-ol, 1-(4-chlorophenyl)-2-(1,2,4-triazol-1-yl)-4,4-dimethyl-1-penten-3-ol and 1-cyclohexyl-2-(1,2,4-triazol-1-yl)-4,4-dimethyl-1-penten-3-ol [Japanese Patent Application Kokai (Laid-open) Nos. 124771/1980, 100547/1979 and 111477/1980]. And, it is also well known that there is a remarkable difference in the activity between the optical isomers, and that, for example, with reference to the foregoing 1-(2,4-dichlorophenyl)-2-(1,2,4-triazol-1-yl)-4,4-dimethyl-1-penten-3-ol and 1-(4-chlorophenyl)-2-(1,2,4-triazol-1-yl)-4,4-dimethyl-1-penten-3-ol, the (−)-isomer has a strong activity as fungicides, while the (+)-isomer has a strong activity as plant growth regulators and herbicides [Japanese Patent Application Kokai (Laid-open) Nos. 99575/1982 and 106669/1982].

For this reason, there is a great demand for the development of a method to produce either one of the (−)- or (+)-optical isomer according to intended uses and yet with a good efficiency in industry.

As the conventionally well-known common reducing agent for reducing the carbonyl group of ketone compounds into alcohol compounds, there are various reagents represented by lithium aluminum hydride and sodium borohydride. The reduction product produced when these reagents are used is an optically inactive, i.e. racemic compound, and when these reagents are used for the reduction of ketone compounds having an unsaturated bond, particularly $\alpha$, $\beta$-conjugated unsaturated ketones like the material used in the method of the present invention, reduction of the double bond in addition to the carbonyl group is easy to occur, and besides there also comes out a possibility that the steric configuration correlated with the double bond is isomerized.

As the conventionally employed method for producing optically active alcohol derivatives by asymmetric reduction, there are the following methods to carry out the asymmetric reduction of ketone compounds with lithium aluminum hydride modified with an optically active compound: A method of using an optically active N-methylephedrine [I. Jacquet, et al., Tetrahedron Letters, 1974, 2065; J. P. Vigneron, et al., Tetrahedron, 32, 939 (1976); J. P. Vigneron, et al., Tetrahedron Letters, 1979, 2683; idem, ibid., 1980, 1735; and Japanese Patent Application Kokai (Laid-open) Nos. 99575/1982 and 106669/1982]; a method of using an optically active proline derivative [M. Asami, et al., Heterocycles, 12, 499 (1979)] and a method of using an optically active binaphthyl derivative [R. Noyori, et al., J. Am. Chem. Soc., 101, 3129 (1979); R. Noyori, et al., ibid., 101, 5843 (1979)].

These methods, however, may not always be said to be satisfactory in industry, for example, in the following points: (1) Since lithium aluminum hydride is used, there is a danger such as ignition by contact with moisture, and (2) in order to obtain an alcohol compound having a higher optical purity, additives such as N-substituted aniline are required in large amounts.

Also, in asymmetric reduction, the following methods are reported as a method for producing optically active alcohols using an asymmetrically modified boron hydride-reducing agent:

(1) A method of using sodium borohydride and the onium salt of optically active ephedrine [described in S. Colona, et al., J. Chem. Soc., Perkin Trans I, 371 (1978)], (2) a method of using an optically active amine-borane complex [described in R. F. Borch, et al., J. Org. Chem. 37, 2347 (1972)], (3) a method of using an α-amino acid ester-borane complex [described in M. F. Grundon, et al., Tetrahedron Letters, 295 (1976)], and (4) a method of the asymmetric reduction of aromatic ketones with an optically active amino alcohol and borane [described in A. Hirao, et al., J. Chem. Soc., Chem. Comm., 315 (1981); S. Itsuno, et al., ibid., 469 (1983); and S. Itsuno et al., J. Chem. Soc. Perkin Trans I, 1673 (1983)].

But, the methods (1), (2) and (3) are too low in optical yield to say that they are a practical method. Also, the method (4) may not always be said to be satisfactory to carry it out in industry because, in order to attain high optical purity, borane of two times by mole, as converted to boron basis, as much as amino alcohol is required.

DISCLOSURE OF INVENTION

In view of the situation like this, the present inventors extensively studied a method for obtaining the optically active alcohol derivative represented by the formula (III) by the asymmetric reduction of the ketone compound represented by the above formula (II), and as a result, found that, by using an asymmetrically modified boron hydride compound (hereinafter referred to as present compound) obtained by reacting the optically active amino alcohol represented by the above formula (I) or its salt with an acid with a boron hydride compound, only the carbonyl group is selectively reduced into the objective optically active alcohol derivative with safety as well as good efficiency.

Next, the present invention will be illustrated.

In the optically active amino alcohol represented by the above formula (I), a material for the present compound, specific examples of a substituent $R_1$ include a $C_1$-$C_{10}$ alkyl, $C_5$-$C_{10}$ cycloalkyl and $C_7$-$C_{16}$ aralkyl groups, a phenyl group which may be substituted with a halogen atom or an alkyl, cyano, alkoxyl or alkoxycarbonyl group, and a naphthyl group which may be substituted with a halogen atom or an alkyl, cyano, alkoxyl or alkoxycarbonyl group. Specific examples of $R_2$ include a $C_6$-$C_{16}$ aryl, $C_1$-$C_{10}$ alkyl and $C_7$-$C_{16}$ aralkyl groups and an alkyloxycarbonyl group in which the number of carbon atoms constituting the alkyl group is 1 to 10. Specific examples of $R_3$ include a hydrogen atom, a $C_1$-$C_6$ alkyl and $C_7$-$C_{16}$ aralkyl groups. More specifically, as the optically active amino alcohol represented by the formula (I), there may be given norephedrine, norpseudoephedrine, threonine ester, 1,2-diphenyl-2-amino-1-ethanol, 1-(2,5-dimethylphenyl)-2-amino-1-propanol and 1-α-naphthyl-2-amino-1-propanol. These optically active amino alcohols are produced, for example, by the methods described in M. J. Kalm, J. Org. Chem., 25, 1929–37 (1960); W. H. Hartung, et al., J. Am. Chem. Soc., 52, 3317–22 (1930); W. H. Hartung, et al., J. Am. Chem. Soc., 51, 2262–6 (1929); M. C. Kloetzel, et al., J. Org. Chem., 11, 390–4 (1946), and the like.

In the present invention, the halogen atom represents fluorine atom, chlorine atom or bromine atom.

Next, reference will be made to a method for producing the present compound.

The present compound, when the boron hydride compound is a metal borohydride, is obtained by reacting a salt, as obtained from the optically active amino alcohol represented by the formula (I) and an acid, with the metal borohydride in a solvent, or when the borohydride copound is a borane, it is obtained by directly reacting the optically active amino alcohol represented by the formula (I) with the borane in a solvent. As the foregoing acid which is a material for producing the salt of the optically active amino alcohol, there are given mineral acids (e.g. hydrochloric acid, sulfuric acid, nitric acid, phosphoric acid, carboxylic acids (e.g. acetic acid), organic sulfonic acids (e.g. p-toluenesulfonic acid) and the like. Said salt may be used as such or may be produced, in situ, from the optically active amino alcohol and the acid in the reaction system for producing the present reducing agent.

As the metal borohydride described above, there are given for example sodium borohydride, potassium borohydride, lithium borohydride, zinc borohydride, etc. Generally, however, the object of the present invention can sufficiently be achieved by using easily available sodium borohydride. As the borane, for example diborane, boranetetrahydrofuran complex, borane-dimethyl sulfide complex, etc. may be given.

In production of the present compound, the molar ratio of the borohydride compound to the optically active amino alcohol is, when said compound is a metal borohydride, 0.7:1 to 2:1, preferably 0.7:1 to 1.3:1, more preferably 1 to 1, as converted to boron basis, and when said compound is a borane, said molar ratio is 0.7:1 to 1.3:1, preferably 1 to 1.

The solvent used in producing the present compound is not particularly limited, so long as it does not take part in the reaction. For example, however, there are given aromatic hydrocarbons (e.g. benzene, toluene, xylene, chlorobenzene), halogenated hydrocarbons (e.g. methylene chloride, 1,2-dichloroethane, chloroform, carbon tetrachloride), and mixtures thereof. When the metal borohydride is used, in order to solve it, for example dimethyl sulfoxide, diglyme, dimethylformamide, 1,3-dimethyl-2-imidazolidinone or the like may be used in combination. The reaction temperature is generally within a range of −78° to 100° C., preferably −40° to 100° C. The reaction is generally carried out in an inert gas atmosphere such as nitrogen, argon, etc.

Also, by decomposing the present compound with an aqueous alkali solution, a compound represented by the formula (V),

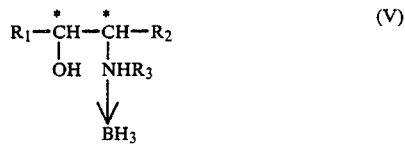

wherein $R_1$, $R_2$, $R_3$ and a mark * have the same meanings as above, is obtained.

The present compound thus obtained may be used for the subsequent reduction after separated from the reaction solution, but generally, it is used as the solution without being separated therefrom.

Next, reference will be made to a method for producing the optically active alcohol derivative of the above formula (III) by reduction of the ketone compound represented by the above formula (II) using the present compound thus obtained.

The amount of the present compound used in the reduction is not less than 0.5 mole, generally within a range of 1 to 5 moles, as converted to boron basis, based on 1 mole of the ketone compound represented by the formula (II), and even the range of 1 to 2 moles can sufficiently achieve the object.

Also, the solvent used in the foregoing reduction is not particularly limited, so long as it is an inactive solvent. Preferably, however, organic solvents such as aromatic hydrocarbons (e.g. benzene, toluene, xylene, chlorobenzene), halogenated hydrocarbons (e.g. methylene chloride, 1,2-dichloroethane, chloroform, carbon tetrachloride), ethers (e.g. diethyl ether, tetrahydrofuran, dioxane, diglyme) and mixtures thereof are used. Also, the solvent used in producing the present compound may be used as it is or in mixture with the solvents described above. The reduction is generally carried out in an inert gas atmosphere as described above. The temperature of the reduction is generally within a range of $-30°$ to $100°$ C., and industrially within a range of $-10°$ to $50°$ C.

The foregoing reduction may be carried out in the presence of an acid, and particularly when sodium borohydride is used as a material for the present compound, isomerization between the E form and Z form of the ketone compound represented by the above formula (I) is inhibited, whereby the yield of the objective optically active alcohol derivative can be increased. As the acid, there are given for example Lewis acids (e.g. titanium tetrachloride, boron trifluoride etherate, aluminum chloride), carboxylic acids (e.g. acetic acid, chloroacetic acid, propionic acid) and mineral acids (e.g. hydrochloric acid, sulfuric acid, phosphoric acid). The molar ratio of these acids to the ketone compound is generally within a range of 0.01:1 to 1:1, preferably 0.01:1 to 0.5:1.

After the reduction is carried out in this way, the aqueous solution of a mineral acid (e.g. hydrochloric acid, sulfuric acid) is generally added to the reaction solution, the organic layer is separated from the aqueous layer, washed with water and dried, and then the organic solvent is removed by evaporation. By this procedure, the objective aforementioned optically active alcohol derivative represented by the formula (III) is obtained in a high yield.

The optical purity is obtained by measuring the optical rotation of the product obtained, or directly measuring the enantiomer ratio by high-performance liquid chromatography with optically active packing materials.

Hereupon, the optically active amino alcohol used can easily be recovered, with its steric configuration maintained, by adding an aqueous alkali solution to the aqueous layer after the reaction and extracting with an organic solvent. The recovered optically active amino alcohol can be re-used.

BEST MODE FOR CARRYING OUT THE INVENTION

Example 1

In a nitrogen atmosphere, 0.338 g of (+)-norephedrine hydrochloride was suspended in 5 ml of deutero chloroform, and after cooling to $-30°$ C., a solution of 0.0681 g of sodium borohydride in 1 ml of dimethylformamide was added. On raising the temperature of the resulting mixture from $-30°$ C. to room temperature over 2 hours, 87 ml of hydrogen gas was generated to obtain a solution of the present compound. $^{11}$B nuclear magnetic resonance spectrum (standard, BF$_3$.O-

Et$_2$) of this solution was as follows: $-20.95$ ppm, $+7.21$ ppm.

Thereafter, this solution was decomposed with 2.5N aqueous sodium hydroxide solution, and the organic layer was washed with water and purified by column chromatography on silica gel with a n-hexane/ethyl acetate (1:1) mixture as a developing solvent to obtain 0.112 g of a crystal.

$^{11}$B nuclear magnetic resonance spectrum (standard, BF$_3$.OEt$_2$): $-20.5$ ppm
m.p. $93°-95°$ C. (dec.)

This crystal, as a result of X-ray diffraction analysis, was identified to be a borohydride compound having the following structure:

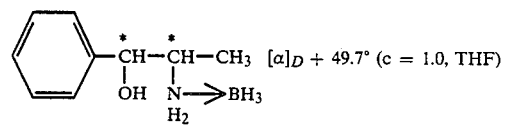

Example 2

Reaction was carried out in the same manner as in Example 1 except that dimethylformamide was replaced by deutero dimethylformamide, to obtain a solution of the present compound having the following physical property:

$^1$H nuclear magnetic resonance spectrum [CDCl$_3$-DMF-d$_7$, $\delta$(ppm)]: 0.97(d), 1.04(d), 2.75–3.15(m), 3.1–3.5(broad), 4.2–4.7(broad), 5.18(d), 7.31(s)

Examples 3 and 4

Reaction was carried out in the same manner as in Example 2 except that (+)-norephedrine hydrochloride was replaced by (+)-1-(2,5-dimethylphenyl)-2-amino-1-propanol hydrochloride and (−)-1-α-naphthyl-2-amino-1-propanol hydrochloride, to obtain a solution of the present compound having the physical property shown in Table 1.

TABLE 1

| Example No. | $^{11}$B NMR spectrum [$\delta$(ppm)] |
|---|---|
| 3 | $-20.6, +6.5$ |
| 4 | $-20.3, +6.4$ |

Example 5

In a nitrogen atmosphere, a solution of 0.272 g (1.8 mmoles) of (+)-norephedrine in 4 ml of 1,2-dichloroethane was added dropwise at $-78°$ C. to a solution comprising 1.8 ml (0.9 mmole) of a 0.50M diborane-tetrahydrofuran solution and 2 ml of 1,2-dichloroethane, and the temperature of the resulting mixture was raised from $-78°$ C. to room temperature over about 2 hours. $^{11}$B nuclear magnetic resonance spectrum of this solution was as follows: $-20.7$ ppm, $+7.7$ ppm.

Example 6

In a nitrogen atmosphere, 0.338 g (1.8 mmoles) of (+)-norephedrine hydrochloride was suspended in 5 ml of 1,2-dichloroethane, and after cooling to $-30°$ C., a solution of 0.0681 g (1.8 mmoles) of sodium borohydride in 1 ml of dimethylformamide was added. On raising the temperature of the resulting suspension from $-30°$ C. to room temperature over 2 hours, 87 ml of hydrogen gas was generated. Thereafter, a solution of 0.39 g (1.2 mmoles) of (E)-1-(2,4-dichlorophenyl)-2-(1,2,4-triazol-1-yl)-4,4-dimethyl-1-penten-3-one (E/Z=99.9/0.1) in 4 ml of 1,2-dichloroethane was added to this suspension at room temperature, and then stirring was carried out for 23 hours. Thereafter, 6 ml of 2M hydrochloric acid was added, followed by stirring for 2 hours. The organic layer was washed with water, dried and concentrated under reduced pressure. The residue was purified on a column packed with 2 g of silica gel with a chloroform solvent and then concentrated under reduced pressure to obtain 0.39 g of (−)-(E)-1-(2,4-dichlorophenyl)-2-(1,2,4-triazol-1-yl)-4,4-dimethyl-1-penten-3-ol as a crude crystal. By gas-chromatographic analysis, it was found that the conversion was 96.4%, and the composition of the reaction product was: E-form alcohol, 98.3% and Z-form alcohol, 1.7% (Z-form alcohol was produced through isomerization of the ketone compound to the Z-form, followed by reduction of the carbonyl group).

Optical rotation $[\alpha]_D$: −19.93° (c=1.0, CHCl$_3$)

By high-performance liquid-chromatographic analysis using an optically active column, it was found that the enantiomer ratio of the E-form alcohol was: (−)-isomer, 85.1% and (+)-isomer, 14.9%. The optical yield was 70.2%.

Examples 7 to 10

Reaction was carried out according to Example 6 using the reaction solvents described below in place of 1,2-dichloroethane, to obtain (−)-(E)-1-(2,4-dichlorophenyl)-2-(1,2,4-triazol-1-yl)-4,4-dimethyl-1-penten-3-ol.

The results are shown in Table 2. In the table, the solvents in parentheses in the column, "Reaction solvent", are a solvent used for dissolving sodium borohydride.

TABLE 2

| Example No. | Reaction solvent | Reduction time (hr) | Conversion (%) | Reaction product E-form alcohol (%) | Reaction product Z-form alcohol (%) | Enantiomer ratio(−/+) of E-form alcohol | Optical yield of E-form alcohol (%) |
|---|---|---|---|---|---|---|---|
| 7 | 1,2-Dichloroethane (diglyme) | 25 | 94.9 | 98.8 | 1.2 | 83.5/16.5 | 67 |
| 8 | 1,2-Dichloroethane (dimethyl sulfoxide) | 43 | 93.7 | 97.0 | 3.0 | 80/20 | 60 |
| 9 | Toluene (dimethylformamide) | 25 | 97.4 | 96.8 | 3.2 | 78/22 | 56 |
| 10 | Chlorobenzene (dimethylformamide) | 72 | 99.9 | 97.1 | 2.9 | 80.5/19.5 | 61 |

Examples 11 to 13

Reaction was carried out according to Example 6 using (E)-1-(4-chlorophenyl)-2-(1,2,4-triazol-1-yl)-4,4-dimethyl-1-penten-3-one (E/Z=99.8/0.2) in place of (E)-1-(2,4-dichlorophenyl-2-(1,2,4-triazol-1-yl)-4,4-dimethyl-1-penten-3-one and at varying molar ratios, 1.0, 1.1 and 1.2, of sodium borohydride to norephedrine hydrochloride. The results are shown in Table 3. Hereupon the saturated alcohol of the reaction products means a product obtained by hydrogenation of both the carbonyl group and the carbon/carbon double bond contained in the ketone compound which is a material.

TABLE 3

| Example No. | Molar ratio of sodium borohydride to norephedrine hydrochloride | Reaction time (hr) | Conversion (%) | Reaction product E-form alcohol (%) | Reaction product Saturated alcohol (%) | Reaction product Z-form alcohol (%) | Enantiomer ratio(−/+) of E-form alcohol | Optical yield of E-form alcohol (%) |
|---|---|---|---|---|---|---|---|---|
| 11 | 1.0 | 24.0 | 97.5 | 83.7 | 0.4 | 15.9 | 81.1/18.9 | 62.2 |
| 12 | 1.1 | 67.5 | 99.9 | 79.3 | 1.4 | 19.2 | 82.3/17.7 | 64.6 |
| 13 | 1.2 | 15.5 | 96.7 | 64.1 | 13.8 | 22.1 | 83.5/16.5 | 67.0 |

Examples 14 and 15

In a nitrogen atmosphere, a solution of 1.8 mmoles of the following each acid in 1 ml of 1,2-dichloroethane was added to a solution of 0.272 g (1.8 mmoles) of (+)-norephedrine in 4 ml of 1,2-dichloroethane, and after cooling to −30° C., a solution of 0.0681 g (1.8 mmoles) of sodium borohydride in 1 ml of dimethylformamide was added. The temperature of the resulting mixture was raised from −30° C. to room temperature over 2 hours to prepare the present compound. Thereafter, asymmetric reduction of the ketone compound was carried out in the same manner as in Example 6. The results are shown in Table 4.

TABLE 4

| Example No. | Acid | Conversion (%) | Reaction product | | | Enantiomer ratio(−/+) of E-form alcohol | Optical yield of E-form alcohol (%) |
|---|---|---|---|---|---|---|---|
| | | | E-form alcohol (%) | Saturated alcohol (%) | Z-form alcohol (%) | | |
| 14 | Acetic acid | 92.8 | 98.5 | 1.0 | 0.5 | 81.5/18.5 | 63 |
| 15 | p-Toluene-sulfonic acid monohydrate | 91.8 | 94.7 | — | 5.3 | 72/28 | 44 |

Example 16

Reaction was carried out on a scale of ten times that of Example 6. In a nitrogen atmosphere, a solution of 0.681 g (0.018 mole) of sodium borohydride in 9.44 g of dimethylformamide was added dropwise at −20° C. to a suspension of 3.38 g (0.018 mole) of (+)-norephedrine hydrochloride in 62.8 g of 1,2-dichloroethane, and the temperature of the resulting mixture was raised from −20° C. to room temperature over 2 hours. Thereafter, a solution of 3.89 g (0.012 mole) of (E)-1-(2,4-dichlorophenyl)-2-(1,2,4-triazol-1-yl)-4,4-dimethyl-1-penten-3-one (E/Z=97.6/2.4) in 50.24 g of 1,2-dichloroethane was added, and stirring was carried out at room temperature for 21 hours and then at 40° C. for 3 hours. The reaction solution was decomposed with addition of 7.22 g of 10% hydrochloric acid and 2.1 g of water, and the organic layer was separated, washed with water and concentrated under reduced pressure to obtain 3.89 g of (−)-(E)-1-(2,4-dichlorophenyl)-2-(1,2,4-triazol-1-yl)-4,4-dimethyl-1-penten-3-ol as a crystal. The conversion of 99.9%, and the composition of the product obtained was: E-form alcohol, 95.8%; saturated alcohol, 0.2%; Z-form alcohol, 3.5%; and others, 0.5%. The enantiomer ratio of the E-form alcohol was: (−)-isomer, 85.2% and (+)-isomer, 14.8%. The optical yield was 70.4%.

Example 17

Reaction was carried out in the same manner as in Example 16 except that the amounts of 1,2-dichloroethane, a solvent, used were reduced to 13.52 g and 12.2 g from 62.8 g and 50.24 g, respectively. The conversion was 99.9%, and the composition of the product obtained was: E-form alcohol, 88.9%; saturated alcohol, 0.9%; Z-form alcohol, 9.4%; and others, 0.8%. The enantiomer ratio of the E-form alcohol was: (−)-isomer, 84.1% and (+)-isomer, 15.9%. The optical yield was 68.2%.

Examples 18 to 24

Asymmetric reduction of each of (E)-1-(2,4-dichlorophenyl)-2-(1,2,4-triazol-1-yl)-4,4-dimethyl-1-penten-3-one (E/Z=97.6/2.4) and (E)-1-(4-chlorophenyl)-2-(1,2,4-triazol-1-yl)-4,4-dimethyl-1-penten-3-one (E/Z=98.9/1.1) was carried out according to Example 6 using the hydrochloride of each optically active amino alcohol described below in place of (+)-norephedrine hydrochloride. The results are shown in Table 5.

TABLE 5
| Example No. | Ketone compound | Optically active amino alcohol | Reaction time (hr) | Conversion (%) | Reaction product E-form alcohol (%) | Saturated alcohol (%) | Z-form alcohol (%) | Enantiomer ratio (−/+) of E-form alcohol | Optical yield of E-form alcohol (%) |
|---|---|---|---|---|---|---|---|---|---|
| 18 | 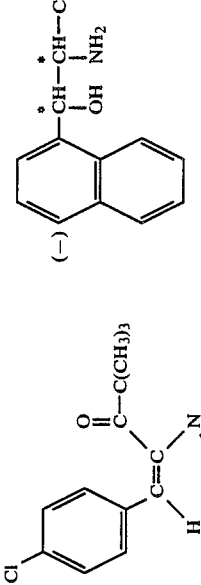 | 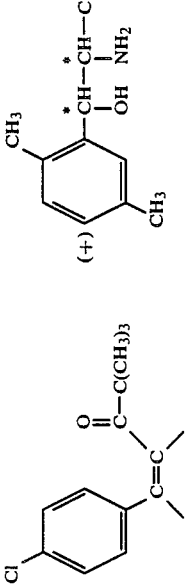 | 69 | 98.7 | 93.6 | <0.1 | 6.3 | 95.9/4.1 | 91.8 |
| 19 | 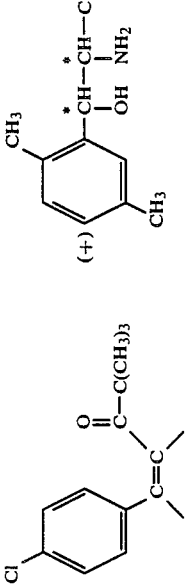 |  | 50 | 88.4 | 92.4 | <0.1 | 7.5 | 10.6/89.4 | 78.8 |
| 20 | 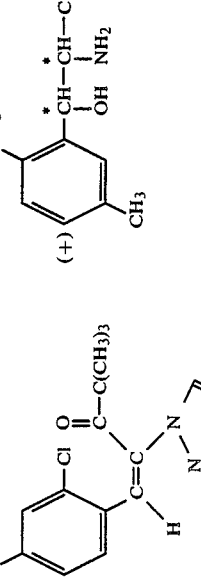 | 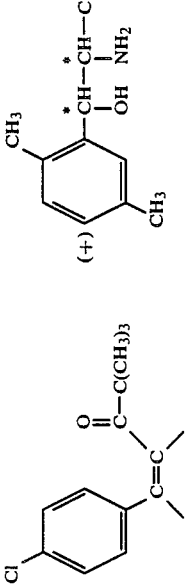 | 69 | 99.9 | 96.6 | <0.1 | 3.3 | 90.2/9.8 | 80.4 |

TABLE 5-continued

| Example No. | Ketone compound | Optically active amino alcohol | Reaction time (hr) | Conversion (%) | E-form alcohol (%) | Saturated alcohol (%) | Z-form alcohol (%) | Enantiomer ratio (−/+) of E-form alcohol | Optical yield of E-form alcohol (%) |
|---|---|---|---|---|---|---|---|---|---|
| 21 | 2,4-Cl-C₆H₃-C(=CH)-C(N-imidazolyl)-C(O)-C(CH₃)₃ | (−) 1-naphthyl-CH(OH)-CH(NH₂)-CH₃ | 50 | 97.8 | 96.1 | <0.1 | 3.8 | 11.0/89.0 | 78.0 |
| 22 | 2,4-Cl-C₆H₃-C(=CH)-C(N-imidazolyl)-C(O)-C(CH₃)₃ | (−) phenyl-CH(OH)-CH(NH₂)-CH₃ (norpseudoephedrine) | 24 | 85.0 | 94.7 | — | 5.3 | 23.5/76.5 | 53.0 |
| 23 | 2,4-Cl-C₆H₃-C(=CH)-C(N-imidazolyl)-C(O)-C(CH₃)₃ | (+) phenyl-CH(OH)-CH(NH₂)-phenyl | 24 | 97.1 | 97.2 | 1.4 | 1.4 | 66.5/33.5 | 33.0 |

TABLE 5-continued
| Example No. | Ketone compound | Optically active amino alcohol | Reaction time (hr) | Conversion (%) | Reaction product | | | Enantiomer ratio (−/+) of E-form alcohol | Optical yield of E-form alcohol (%) |
| --- | --- | --- | --- | --- | --- | --- | --- | --- | --- |
| | | | | | E-form alcohol (%) | Saturated alcohol (%) | Z-form alcohol (%) | | |
| 24 | 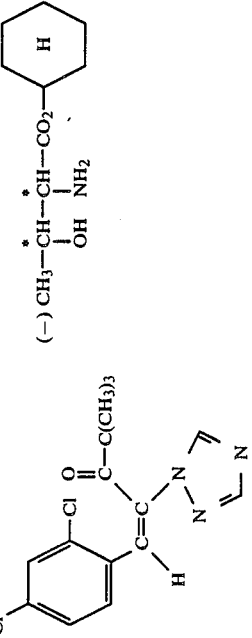 | 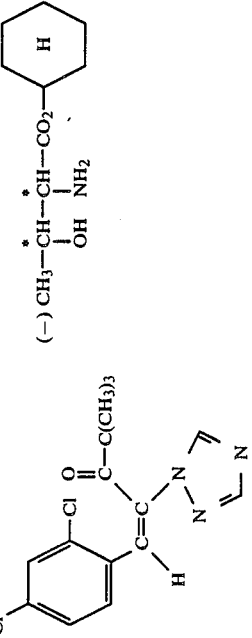 | 24 | 53.6 | 89.6 | 1.1 | 9.3 | 31.7/68.3 | 36.6 |

Examples 25 to 29

Reaction was carried out in the same manner as in Example 6 except that the (E) and (Z) forms of 1-cyclohexyl-4,4-dimethyl-2-(1,2,4-triazol-1-yl)-1-penten-3-one (the E/Z ratios of the former and the latter were 99.9/0.1 and 0.1/99.9, respectively) were used in place of (E)-1-(2,4-dichlorophenyl)-2-(1,2,4-triazol-1-yl)-4,4-dimethyl-1-penten-3-one, and that the hydrochlorides of the optically active amino alcohols and the solvents (solvents in parentheses are a solvent used for dissolving sodium borohydride) described below were used. The results are shown in Table 6.

temperature over 2 hours. Thereafter, to this suspension was added at room temperature a solution of 0.0108 g (0.18 mmole) of acetic acid and 0.35 g (1.2 mmoles) of (E)-1-(4-chlorophenyl)-2-(1,2,4-triazol-1-yl)-4,4-dimethyl-1-penten-3-one (E/Z=99.8/0.2) in 4 ml of 1,2-dichloroethane. The subsequent treatment was carried out according to Example 6.

The conversion was 79.4%, and the composition of the product obtained was: E-form alcohol, 92.5%; saturated alcohol, 0.3%; and Z-form alcohol, 7.2%. The enantiomer ratio of the E-form alcohol was: (−)-isomer, 76.1% and (+)-isomer, 23.9%. The optical yield was 52.2%.

TABLE 6

| Example No. | Ketone compound | Optically active amino alcohol | Solvent | Conversion (%) | Alcohol E/Z | Enantiomer ratio (+/−) of E-form alcohol | Optical yield of E-form alcohol (%) |
|---|---|---|---|---|---|---|---|
| 25 | E-form | (+)-2,4-dimethylphenyl-CH(OH)-CH(NH$_2$)-CH$_3$ | 1,2-Dichloroethane (dimethylformamide) | 100 | 97.1/2.9 | 80.9/19.1 | 61.8 |
| 26 | E-form | (−)-naphthyl-CH(OH)-CH(NH$_2$)-CH$_3$ | Chloroform (dimethylformamide) | 100 | 97.6/2.4 | 17.7/82.3 | 64.6 |
| 27 | E-form | (−)-phenyl-CH(OH)-CH(NH$_2$)-CH$_3$ | 1,2-Dichloroethane (dimethylformamide) | 99.5 | 94.9/5.1 | 20.3/79.7 | 59.4 |
| 28 | Z-form | (−)-phenyl-CH(OH)-CH(NH$_2$)-CH$_3$ | 1,2-Dichloroethane (dimethylformamide) | 100 | 2.0/98.0 | −10.7°[1] | — |
| 29 | Z-form | (+)-phenyl-CH(OH)-CH(NH$_2$)-CH$_3$ | 1,2-Dichloroethane (dimethylformamide) | 100 | 1.2/98.8 | +9.9°[1] | — |

[1] Specific rotation of the product (c = 1.0, CHCl$_3$)

Example 30

In a nitrogen atmosphere, 0.338 g (1.8 mmoles) of (+)-norephedrine hydrochloride was suspended in 5 ml of 1,2-dichloroethane, and to this suspension was added at −30° C. a solution of 0.0681 g (1.8 mmoles) of sodium borohydride in 1 ml of dimethylformamide. The temperature of the resulting suspension was raised to room

Examples 31 to 38

Reaction was carried out according to Example 30 using titanium tetrachloride, boron trifluoride etherate, monochloroacetic acid, propionic acid and conc. sulfuric acid in place of acetic acid. The results are shown in Table 7.

TABLE 7

| Example No. | Lewis acid, carboxylic acid or mineral acid Name | Amount (g) | Molar ratio (%) of acid to amino alcohol | Reaction time (hr) | Conversion (%) | E-form alcohol (%) | Saturated alcohol (%) | Z-form alcohol (%) | Enantiomer ratio (−/+) of E-form alcohol | Optical yield of E-form alcohol (%) |
|---|---|---|---|---|---|---|---|---|---|---|
| 31 | Titanium tetrachloride | 0.017 | 5 | 24 | 63.7 | 96.6 | 0.3 | 3.1 | 66.3/33.7 | 32.6 |
| 32 | Titanium tetrachloride | 0.009 | 2.5 | 24 | 84.4 | 92.6 | 0.1 | 7.3 | 76.8/23.2 | 53.6 |
| 33 | Boron trifluoride etherate | 0.128 | 50 | 23 | 51.1 | 98.5 | 0.6 | 0.9 | 64.2/36.8 | 28.4 |
| 34 | Boron trifluoride etherate | 0.026 | 10 | 24 | 87.7 | 87.6 | 0.2 | 12.2 | 81.3/18.7 | 62.6 |
| 35 | Monochloroacetic acid | 0.017 | 10 | 21 | 68.3 | 91.2 | 0.3 | 8.5 | 69.3/30.7 | 38.6 |
| 36 | Propionic acid | 0.013 | 10 | 68 | 89.1 | 89.1 | — | 10.9 | 67.6/32.4 | 35.2 |
| 37 | Conc. sulfuric acid | 0.018 | 10 | 69 | 92.4 | 90.2 | — | 9.8 | 74.3/25.7 | 48.6 |
| 38 | Conc. sulfuric acid | 0.009 | 5 | 24 | 83.2 | 89.8 | — | 10.2 | 79.2/20.8 | 58.4 |

TABLE 7-continued

| Example No. | Lewis acid, carboxylic acid or mineral acid | | | Reaction time (hr) | Conversion (%) | Reaction product | | | Enantiomer ratio(−/+) of E-form alcohol | Optical yield of E-form alcohol (%) |
|---|---|---|---|---|---|---|---|---|---|---|
| | Name | Amount (g) | Molar ratio (%) of acid to amino alcohol | | | E-form alcohol (%) | Saturated alcohol (%) | Z-form alcohol (%) | | |
| | acid | | | | | | | | | |

Examples 39 to 41

Reaction was carried out according to Example 30 using varying molar ratios of sodium borohydride to norephedrine hydrochloride. The results are shown in Table 8.

TABLE 8

| Example No. | Molar ratio (%) of acetic acid to amino alcohol | Molar ratio (%) of sodium borohydride to norephedrine hydrochloride | Reaction time (hr) | Conversion (%) | Reaction product | | | Enantiomer ratio (−/+) of E-form alcohol | Optical yield of E-form alcohol (%) |
|---|---|---|---|---|---|---|---|---|---|
| | | | | | E-form alcohol (%) | Saturated alcohol (%) | Z-form alcohol (%) | | |
| 39 | 15 | 1.1 | 24 | 90.0 | 92.1 | — | 7.9 | 79.0/21.0 | 58.0 |
| 40 | 30 | 1.2 | 43 | 97.8 | 83.6 | 0.8 | 13.4 | 85.0/15.0 | 70.0 |
| 41* | 15 | 1.1 | 24 | 97.2 | 91.2 | — | 8.8 | 75.5/24.5 | 51.0 |

*Chlorobenzene was used in place of 1,2-dichloroethane.

Example 42

In a nitrogen atmosphere, 0.393 g (0.0065 mole) of acetic acid was added to a suspension of 8.18 g (0.0436 mole) of (−)-norephedrine hydrochloride in 62.17 g of chlorobenzene, and then a solution of 1.815 g (0.0480 mole) of sodium borohydride in 9.35 g of dimethylformamide was added dropwise to this suspension at 5° to 10° C. for 1.5 hours. Thereafter, the resulting mixture was stirred at room temperature for 1 hour, and then a solution of 8.42 g (0.0291 mole; E/Z=99.8/0.2) of (E)-1-(4-chlorophenyl)-2-(1,2,4-triazol-1-yl)-4,4-dimethyl-1-penten-3-one in 49.7 g of chlorobenzene was added at room temperature. The resulting mixture was stirred at the same temperature for 18 hours. The reaction solution was decomposed with addition of 17.50 g of 10% hydrochloric acid and 5 g of water, and the organic layer was separated, washed with water and concentrated under reduced pressure to obtain 8.15 g (+)-(E)-1-(4-chlorophenyl)-2-(1,2,4-triazol-1-yl)-4,4-dimethyl-1-penten-3-ol as a crystal. The conversion was 99.8%, and the composition of the product obtained was: E-form alcohol, 90.8%; saturated alcohol, 2.3%; and Z-form alcohol, 6.9%. The enantiomer ratio of the E-form alcohol was: (+)-isomer, 81.0% and (−)-isomer, 19.0%. The optical yield was 62.0%.

Example 43

In a nitrogen atmosphere, a solution of 2.64 g (0.0698 mole) of sodium borohydride in 14.95 g of dimethylformamide was added dropwise at −20° C. to a suspension of 13.07 g (0.0696 mole) of (+)-norephedrine hydrochloride in 52.26 g of 1,2-dichloroethane, and the temperature of the resulting mixture was raised from −20° C. to room temperature over 2 hours.

Thereafter, 0.35 g of phosphoric acid and then a solution of 16.12 g (0.0497 mole) of (E)-1-(2,4-dichlorophenyl)-2-(1,2,4-triazol-1-yl)-4,4-dimethyl-1-penten-3-one (E/Z=97.6/2.4) in 49.37 g of 1,2-dichloroethane were added at 20° to 25° C., and stirring was carried out at the same temperature for 20 hours. The reaction solution was decomposed with addition of 24.17 g of 20% nitric acid and 4.6 g of water, and the organic layer was separated, washed with water and concentrated under reduced pressure to obtain 15.60 g of (−)-(E)-1-(2,4-dichlorophenyl)-2-(1,2,4-triazol-1-yl)-4,4-dimethyl-1-penten-3-ol as a crystal. The conversion was 99.8%, and the composition of the product obtained was: E-form alcohol, 95.6%; saturated alcohol, 0.4%; Z-form alcohol, 3.2%; and others, 0.8%. The enantiomer ratio of the E-form alcohol was: (−)-isomer, 85.8% and (+)-isomer, 14.2%. The optical yield was 71.6%.

Example 44

In a nitrogen atmosphere, 0.338 g (1.8 mmoles) of (−)-norephedrine hydrochloride was suspended in a mixture comprising 15.4 μl (0.27 mmole) of acetic acid and 5 ml of 1,2-dichloroethane, and after cooling to −30° C., a solution of 0.0749 g (1.98 mmoles) of sodium borohydride in 1 ml of dimethylformamide was added. The temperature of the resulting suspension was raised from −30° C. to room temperature over 2 hours. Thereafter, to this suspension was added at room temperature a solution of 0.31 g (1.2 mmoles) of (E)-1-cyclohexyl-4,4-dimethyl-2-(1,2,4-triazol-1-yl)-1-penten-3-one (E/Z=99.9/0.1) and 10.3 μl (0.18 mmole) of acetic acid in 1,2-dichloroethane, and stirring was carried out for 24 hours. The subsequent treatment was carried out in the same manner as in Example 6 to obtain (−)-(E)-1-cyclohexyl-4,4-dimethyl-2-(1,2,4-triazol-1-yl)-1-penten-3-ol. The conversion was 100%, and the composition of the product obtained was: E-form alcohol, 97.4% and Z-form alcohol, 2.6%. The enantiomer ratio of the E-form alcohol was: (−)-isomer, 77.7% and (+)-isomer, 22.3%.

Example 45

In a nitrogen atmosphere, a solution of 0.272 g of (+)-norephedrine in 4 ml of 1,2-dichloroethane was added dropwise at −78° C. to a mixture comprising 1.8 ml of a 0.500M diborane-tetrahydrofuran solution and 2 ml of 1,2-dichloroethane, and the temperature of the resulting mixture was raised from −78° C. to room temperature over about 2 hours. Thereafter, to this solution was added dropwise at room temperature a solution of 0.39 g of (E)-1-(2,4-dichlorophenyl)-2-(1,2,4-triazol-1-yl)-4,4-dimethyl-1-penten-3-one (E/Z=99.9/0.1) in 4 ml of 1,2-dichloroethane, and stirring was carried out for 24 hours. Thereafter, 6 ml of 2M hydrochloric acid was added to the reaction solution, followed by stirring for about 2 hours. The organic layer was washed with water, dried over anhydrous sodium sulfate and concentrated under reduced pressure. The residue was purified on a column packed with 2 g of silica gel using a chloroform solvent and then concentrated under reduced pressure to obtain 0.39 g of (−)-(E)-1-(2,4-dichlorophenyl)-2-(1,2,4-triazol-1-yl)-4,4-dimethyl-1-penten-3-ol as a crude crystal. The conversion was 98.6%, and the composition of the product obtained was: E-form alcohol, 98.6% and Z-form alcohol, 1.4%.

Optical rotation $[\alpha]_D$: −20.7° (c=1.0, CHCl$_3$)

Optical yield of E-form alcohol: 70%

Examples 46 to 50

Reaction was carried out according to Example 45 using the following reaction solvents in place of 1,2-dichloroethane, to obtain (−)-(E)-1-(2,4-dichlorophenyl)-2-(1,2,4-triazol-1-yl)-4,4-dimethyl-1-penten-3-ol. The results are shown in Table 9.

Examples 51 and 52

Reaction was carried out in the same manner as in Example 45 except that toluene was used as reaction solvent in place of 1,2-dichloroethane, the reaction time was changed to 23 hours, and that the molar ratio of diborane to (+)-norephedrine was varied, to obtain (−)-(E)-1-(2,4-dichlorophenyl)-2-(1,2,4-triazol-1-yl)-4,4-dimethyl-1-penten-3-ol. The results are shown in Table 10.

TABLE 10

| | | Reaction product | | | | |
|---|---|---|---|---|---|---|
| Example No. | Diborane/(+)-norephedrine (molar ratio) | Conversion (%) | E-form alcohol (%) | Z-form alcohol (%) | Enantiomer ratio (−/+) of E-form alcohol | Optical yield of E-form alcohol (%) |
| 51 | 0.375/1.0 | 99.4 | 98.5 | 1.5 | 77/23 | 54 |
| 52 | 0.625/1.0 | 99.6 | 99.2 | 0.8 | 76/24 | 52 |

Examples 53 to 57

Reaction was carried out in the same manner as in Example 45 except that the optically active amino alcohols described below were used in place of (+)-norephedrine, and that tetrahydrofuran and diethyl ether were used as a reaction solvent. The results are shown in Table 11.

TABLE 9

| | | | | Reaction product | | |
|---|---|---|---|---|---|---|
| Example No. | Reaction Solvent | Reduction time (hr) | Conversion (%) | E-form alcohol/ Z-form alcohol | Optical rotation $[\alpha]_D$ (c = 1.0, CHCl$_3$) | Optical yield of E-form alcohol (%) |
| 46 | Ethyl ether | 19 | 99.9 | 99.8/0.2 | −16.18° | 54 |
| 47 | Dioxane | 24 | 75.0 | 98.6/1.4 | −14.40° | 64 |
| 48 | Toluene | 21 | 99.5 | 99.4/0.6 | −17.59° | 59 |
| 49 | Methylene chloride | 24 | 99.3 | 99.7/0.3 | −20.50° | 68 |
| 50 | Carbon tetrachloride | 23 | 81.0 | 99.7/0.3 | −13.25° | 55 |

TABLE 11

| | | | | | Reaction product | | | |
|---|---|---|---|---|---|---|---|---|
| Example No. | Optically active amino alcohol | Reaction solvent | Reaction time (hr) | Conversion (%) | E-form alcohol (%) | Z-form alcohol (%) | Enantiomer ratio (−/+) of E-form alcohol | Optical yield of E-form alcohol (%) |
| 53 | L-threonine cyclohexyl ester | Tetrahydrofuran | 117 | 88.6 | 99.9 | 0.1 | 35.4/64.4 | 29.2 |
| 54 | L-threonine cyclohexyl ester | Diethyl ether | 117 | 100 | 99.9 | 0.1 | 33.9/66.1 | 32.2 |
| 55 | L-threonine ethyl ester | Tetrahydrofuran | 24 | 74.4 | 99.3 | 0.7 | 34.9/65.1 | 30.2 |
| 56 | L-threonine ethyl ester | Diethyl ether | 20 | 90.4 | 99.6 | 0.4 | 33.8/66.2 | 32.4 |
| 57 | (+)-1,2-Diphenyl-2-aminoethanol | Tetrahydrofuran | 24 | 83.9 | 98.2 | 1.8 | 68.0/32.0 | 36.0 |

Examples 58 and 59

Reaction was carried out in the same manner as in Example 45 except that (+)-norephedrine was replaced by (−)-norephedrine and (E)-1-(2,4-dichlorophenyl)-2-(1,2,4-triazol-1-yl)-4,4-dimethyl-1-penten-3-one, and that the following ketone compounds were used. The results are shown in Table 12.

(+)-2-amino-1-(2,5-dimethoxyphenyl)-1-propanol hydrochloride, (+)-2-amino-1-(2,5-diethoxyphenyl)-1-propanol hydrochloride, (−)-2-amino-1-(2,4-dimethoxyphenyl)-1-propanol hydrochloride, (+)-2-amino-1-(2-methoxyphenyl)-1-propanol hydrochloride or (−)-2-amino-1-(2-ethoxyphenyl)-1-propanol hydrochloride, to asymmetrically reduce a ketone compound of (E)-1-(4-chlorophenyl)-2-(1,2,4-triazol-1-yl)-4,4-dimethyl-1-

TABLE 12

| Example No. | Ketone compound | Conversion (%) | Reaction product | | | Enantiomer ratio (−/+) of E-form alcohol | Optical yield of E-form alcohol (%) |
|---|---|---|---|---|---|---|---|
| | | | E-form alcohol (%) | Z-form alcohol (%) | Saturated alcohol (%) | | |
| 58 | 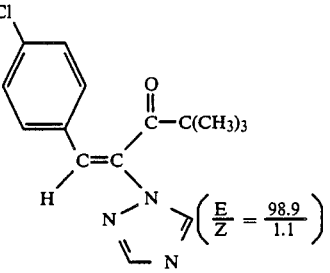 | 97.6 | 96.3 | 3.1 | 0.6 | 15.1/84.9 | 69.8 |
| 59 | 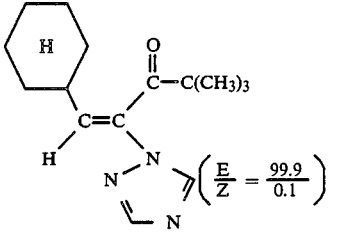 | 100 | 99.0 | 1.0 | — | 73.9/26.1 | 47.8 |

Examples 60 to 69

Asymmetric reduction was carried out in the same manner as in Example 6, except that (+)-norephedrine hydrochloride was replaced by an amino alcohol of penten-3-one (E/Z=98.9/1.1), (E)-1-cyclohexyl-2-(1,2,4-triazol-1-yl)-4,4-dimethyl-1-penten-3-one (E/Z=99.9/0.1) or (E)-1-(2,4-dichlorophenyl)-2-(1,2,4-triazol-1-yl)-4,4-dimethyl-1-penten-3-one (E/Z=97.6/2.4). The results are shown in Table 13.

TABLE 13

| Example No. | Ketone compound | Amino alcohol | Reaction time (hr) | Conversion (%) | Reaction product E-form alcohol (%) | Reaction product Saturated alcohol (%) | Reaction product Z-form alcohol (%) | Enantiomer ratio (−/+) of E-form alcohol | Optical yield of E-form alcohol (%) |
|---|---|---|---|---|---|---|---|---|---|
| 60 | 4-Cl-C6H4-C(=CH-H)-C(N-imidazole)-C(O)-C(CH3)3 | 2-OCH3, 5-CH3O-C6H3-*CH(OH)-*CH(NH2)-CH3 (+) | 24.0 | 99.9 | 95.0 | <0.1 | 4.9 | 94.5/5.5 | 89.0 |
| 61[1] | 4-Cl-C6H4-C(=CH-H)-C(N-imidazole)-C(O)-C(CH3)3 | 2-OCH3, 5-CH3O-C6H3-*CH(OH)-*CH(NH2)-CH3 (+) | 98.0 | 94.2 | 96.2 | <0.1 | 3.7 | 98.1/1.9 | 96.2 |
| 62 | cyclohexyl-C(=CH-H)-C(N-imidazole)-C(O)-C(CH3)3 | 2-OCH3, 5-CH3O-C6H3-*CH(OH)-*CH(NH2)-CH3 (+) | 23.0 | 100.0 | 97.2 | — | 2.8 | 13.0/87.0 | 74.0 |

TABLE 13-continued

| Example No. | Ketone compound | Amino alcohol | Reaction time (hr) | Conversion (%) | Reaction product E-form alcohol (%) | Saturated alcohol (%) | Z-form alcohol (%) | Enantiomer ratio (−/+) of E-form alcohol | Optical yield of E-form alcohol (%) |
|---|---|---|---|---|---|---|---|---|---|
| 63 | (cyclohexyl)C=C(H)(C(=O)C(CH$_3$)$_3$)(imidazolyl) | (+) 2,5-di-OC$_2$H$_5$-phenyl-CH(OH)-CH(NH$_2$)-CH$_3$ | 20.0 | 100.0 | 97.3 | — | 2.7 | 14.9/85.1 | 70.2 |
| 64 | (2,4-diCl-phenyl)C=C(H)(C(=O)C(CH$_3$)$_3$)(imidazolyl) | (+) 2-OCH$_3$-5-OCH$_3$-phenyl-CH(OH)-CH(NH$_2$)-CH$_3$ | 24.0 | 99.9 | 96.9 | <0.1 | 3.0 | 94.7/5.3 | 89.4 |
| 65 | (2,4-diCl-phenyl)C=C(H)(C(=O)C(CH$_3$)$_3$)(imidazolyl) | (+) 2-OC$_2$H$_5$-5-OC$_2$H$_5$-phenyl-CH(OH)-CH(NH$_2$)-CH$_3$ | 24.0 | 99.9 | 96.6 | <0.1 | 3.3 | 90.3/9.7 | 80.6 |

TABLE 13-continued

| Example No. | Ketone compound | Amino alcohol | Reaction time (hr) | Conversion (%) | Reaction product | | | Enantiomer ratio (−/+) of E-form alcohol | Optical yield of E-form alcohol (%) |
|---|---|---|---|---|---|---|---|---|---|
| | | | | | E-form alcohol (%) | Saturated alcohol (%) | Z-form alcohol (%) | | |
| 66 | 2,4-Cl-C6H3-C(=O)-C(C(CH3)3)(imidazolyl)=CH-H | (−) 2-OCH3, 4-OCH3 phenyl CH(OH)-CH(NH2)-CH3 | 26.0 | 97.8 | 95.7 | <0.1 | 4.2 | 11.2/88.8 | 77.6 |
| 67 | 4-Cl-C6H4-C(=O)-C(C(CH3)3)(imidazolyl)=CH-H | (+) 2-OCH3 phenyl CH(OH)-CH(NH2)-CH3 | 69.0 | 98.2 | 90.5 | <0.1 | 9.4 | 97.3/2.7 | 94.6 |
| 68 | 2,4-Cl-C6H3-C(=O)-C(C(CH3)3)(imidazolyl)=CH-H | (+) 2-OCH3 phenyl CH(OH)-CH(NH2)-CH3 | 69.0 | 100.0 | 96.2 | <0.1 | 3.7 | 96.6/3.4 | 93.2 |

TABLE 13-continued
| Example No. | Ketone compound | Amino alcohol | Reaction time (hr) | Conversion (%) | Reaction product | | | Enantiomer ratio (−/+) of E-form alcohol | Optical yield of E-form alcohol (%) |
|---|---|---|---|---|---|---|---|---|---|
| | | | | | E-form alcohol (%) | Saturated alcohol (%) | Z-form alcohol (%) | | |
| 69 | 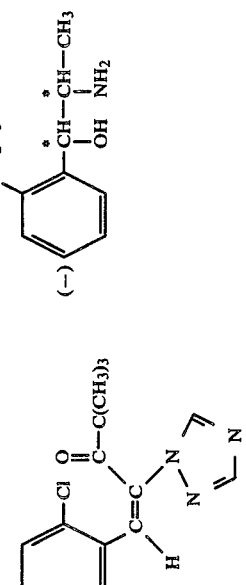 | OC$_2$H$_5$ <br> *CH—*CH—CH$_3$ <br> OH  NH$_2$ <br> (−) | 21.0 | 99.0 | 96.4 | <0.1 | 3.5 | 6.6/93.4 | 86.8 |
¹Reaction temperature is in the range of 10°–12° C. instead of room temperature in Example 6.

Example 70

Under a nitrogen atmosphere, 0.4459 g (1.8 mmoles) of (−)-erythro-2-amino-1-(2,4-dimethoxyphenyl)-1-propanol hydrochloride (optical purity, 98.6%) was suspended in 5 ml of 1,2-dichloroethane, the suspension was cooled to −25° C., and after adding a solution of 0.0681 g (1.8 mmoles) of sodium borohydride in 1 ml of dimethylformamide, the temperature was raised from −25° C. to room temperature over 2.5 hours. Thereafter, to this suspension was added at 20° C. a solution of 0.35 g (1.2 mmoles) of (E)-1-(4-chlorophenyl)-2-(1,2,4-triazol-1-yl)-4,4-dimethyl-1-penten-3-one (E/Z=98.9/1.1) in 4 ml of 1,2-dichloroethane, and the mixture was stirred for 26 hours. Thereafter, decomposition was carried out at 45° C. with stirring with addition of 8 ml of 10% hydrochloric acid. The organic layer was washed with water, dried over anhydrous sodium sulfate and concentrated under reduced pressure to obtain 0.35 g of a crude crystal of (+)-(E)-1-(4-chlorophenyl)-2-(1,2,4-triazol-1-yl)-4,4-dimethyl-1-penten-3-ol. Gas chromatographic analysis showed that the conversion was 97.8% and that the product comprised 95.7% of the E-form alcohol and 4.3% of the Z-form alcohol. High-performance liquid chromatography on optically active column showed that the enantiomer ratio of the E-form alcohol was: (+)-form, 85.0%; and (−)-form, 15.0%.

Reference example 1

To a mixture of 8.43 g (0.04 mole) of (±)-erythro-2-amino-1-(2,4-dimethoxyphenyl)-1-propanol (erythro/threo= 98.9/1.1) and 60 ml of water was added 5.21 g (0.04 mole) of D-(−)-pantolactone, and after stirring at 80° to 90° C. for 1 hour, the reaction solution was concentrated under reduced pressure. The residue obtained was recrystallized from 50 ml of methanol-ethanol (1:4) mixture to obtain 5.44 g of the diastereomer salt of D-(−)-pantoic acid. $[\alpha]_D$: −16.0° (c=1.0, water). This product was recrystallized once more from 50 ml of ethanol to obtain 3.64 g of D-(−)-pantoic acid salt of (−)-erythro-2-amino-1-(2,4-dimethoxyphenyl)-1-propanol. $[\alpha]_D$: −19.4° (c=0.1, water). The diastereomer salt obtained was decomposed with a solution of 1 g of potassium hydroxide in 10 ml of water and extracted with methylene chloride to obtain 2.07 g of (−)-erythro-2-amino-1-(2,4-dimethoxyphenyl)-1-propanol (erythro/threo=99.6/0.4). m.p.: 92°–93° C. The optical purity of this product was 98.6% by high-performance liquid chromatographic analysis. By dissolving this aminoalcohol in a mixed solvent of diethyl ether and methylene chloride and passing a hydrogen chloride gas therethrough, 2.36 g of (−)-erythro-2-amino-1-(2,4-dimethoxyphenyl)-1-propanol hydrochloride was obtained. m.p.: 183°–183.5° C. (decomp.). $[\alpha]_D$: −34.0° (c=1.0, water). The optical purity of this product was 98.6% by high-performance liquid chromatographic analysis.

Reference example 2

A mixture of 14.05 g of (±)-erythro-2-amino-1-(2-methoxyphenyl)-1-propanol (erythro/threo=98.0/2.0), 10.09 g of D-(−)-pantolactone and 100 ml of water was heated for 1 hour with stirring and concentrated under reduced pressure. The residue obtained was recrystallized from 110 ml of isopropanol to obtain 5.09 g of the D-(−)-pantoic acid salt of (+)-erythro-2-amino-1-(2-methoxyphenyl)-1-propanol. $[\alpha]_D$: +22.9° (c=0.9, water). This diastereomer salt was decomposed with a solution of 1.61 g of potassium hydroxide in 20 ml of water and extracted with chloroform to obtain 2.58 g of (+)-erythro-2-amino-1-(2-methoxyphenyl)-1-propanol. By dissolving this aminoalcohol in diethyl ether-chloroform mixture and passing a hydrogen chloride gas therethrough, the hydrochloric acid salt of the aminoalcohol was formed. This salt was collected by filtration and dried to obtain 2.82 g of (+)-erythro-2-amino-1-(2-methoxyphenyl)-1-propanol hydrochloride. $[\alpha]_D$: +26.5° (c=1.0, water). This product was converted to its sugar derivative (diastereomer) and analyzed by high-performance liquid chromatography to find that its optical purity was 62.6%. The filtrate after recrystallization was concentrated under reduced pressure to obtain 20.28 g of the D-(−)-pantoic acid salt of (−)-erythro-2-amino-1-(2-methoxyphenyl)-1-propanol. $[\alpha]_D$: +1.29° (c=1.0, water). This product was recrystallized from isopropanol, and after filtration, the filtrate obtained was concentrated under reduced pressure, decomposed with a solution of 3.76 g of potassium hydroxide in 47 ml of water and extracted with chloroform to obtain 6.79 g of (−)-erythro-2-amino-1-(2-methoxyphenyl)-1-propanol. This aminoalcohol was converted to its sugar derivative (diastereomer) and analyzed by high-performance liquid chromatography to find that its optical purity was 44.6%. By dissolving this aminoalcohol in diethyl ether-chloroform mixture and passing a hydrogen chloride gas therethrough, (−)-erythro-2-amino-1-(2-methoxyphenyl)-1-propanol hydrochloride was obtained. After recrystallizing this hydrochloride three times from ethanol, 1.75 g of (−)-erythro-2-amino-1-(2-methoxyphenyl)-1-propanol hydrochloride was obtained from the filtrate. $[\alpha]_D$: −37.7° (c=1.0, water). The optical purity of this product was 98.0% by high-performance liquid chromagographic analysis.

Reference example 3

On adding a hot solution of 20.5 g (0.0918 mole) of (±)-erythro-2-amino-1-(2,5-diethoxyphenyl)-1-propanol (erythro/threo=98.4/1.6) in 40 ml of methanol to a hot solution of 13.78 g (0.0918 mole) of L-(+)-tartaric acid in 50 ml of methanol, a crystal was deposited. This crystal was re-dissolved in the solution by additionally adding 140 ml of methanol, and after allowing to cool, the deposited crystal was collected by filtration. The yield of the crystal was 12.43 g. $[\alpha]_D$: +28.0° (c=1.0, water). This crystal was further recrystallized from 150 ml of methanol to obtain 7.44 g of the L-(+)-tartaric acid salt of (+)-erythro-2-amino-1-(2,5-diethoxyphenyl)-1-propanol. $[\alpha]_D$: +31.8° (c=1.0, water). This salt was decomposed with a 10% aqueous sodium hydroxide solution and extracted with methylene chloride to obtain 4.75 g of (+)-erythro-2-amino-1-(2,5-diethoxyphenyl)-1-propanol (erythro/threo=100/0). By dissolving this product in diethyl ether and passing a hydrogen chloride gas therethrough, 5.40 g of (+)-erythro-2-amino-1-(2,5-diethoxyphenyl)-1-propanol hydrochloride was obtained. m.p.: 136.5°–138.5° C. $[\alpha]_D$: +29.1° (c=1.0, water). The optical purity of this product was 99.0% or more by high-performance liquid chromatographic analysis.

Reference example 4

A hot solution of 11.19 g of (±)-erythro-2-amino-1-(2-ethoxyphenyl)-1-propanol (content of the erythro-form, 99% or more) in 15 ml of methanol was added to a hot solution of 8.60 g of L-(+)-tartaric acid in 20 ml of methanol, and the resulting solution was allowed to cool. The deposited crystal was collected by filtration to obtain 10.44 g of the L-(+)-tartaric acid salt of (−)-erythro-2-amino-1-(2-ethoxyphenyl)-1-propanol. $[\alpha]_D$: +6.3° (c=1.0, water). This salt was recrystallized from methanol to obtain 4.50 g of a crystal. $[\alpha]_D$: −8.4° (c=1.0, water). This crystal was decomposed with a 20% aqueous sodium hydroxide solution and extracted with chloroform to obtain 2.79 g of (−)-erythro-2-amino-1-(2-ethoxyphenyl)-1-propanol. $[\alpha]_D$: −16.4° (c=1.0, CHCl$_3$). This aminoalcohol was converted to its sugar derivative (diastereomer) and analyzed by high-performance liquid chromatography to find that its optical purity was 63.2%. By dissolving this aminoalcohol in diethyl ether-chloroform mixture and passing a hydrogen chloride gas therethrough, 3.18 g of (−)-erythro-2-amino-1-(2-ethoxyphenyl)-1-propanol hydrochloride was obtained. Recrystallization of this product from isopropanol was repeated four times to obtain 1.02 g of a crystal. $[\alpha]_D$: −43.6° (c=1.0, water). The optical purity of the crystal was 97.8%.

Reference example 5

On adding a solution of 4.56 g (0.0263 mole) of N-acetyl-L-leucine and 1.11 g (0.0263 mole) of 95% sodium hydroxide in 50 ml of water to a solution of 12.17 g (0.0525 mole) of (±)-erythro-2-amino-(2-methoxy-5-methylphenyl)-1-propanol hydrochloride (erythro-form, 99% or more) in 115 ml of water, a crystal was deposited. This crystal was re-dissolved in the solution by additionally adding 500 ml of water, and after allowing to cool, the deposited crystal was collected by filtration. The yield of the N-acetyl-L-leucine salt of (−)-erythro-2-amino-1-(2-methoxy-5-methylphenyl)-1-propanol was 3.63 g. $[\alpha]_D$: −29.2° (c=1.0, water). This salt was decomposed with a 10% aqueous sodium hydroxide solution and extracted with chloroform to obtain 1.94 g of (−)-erythro-2-amino-1-(2-methoxy-5-methylphenyl)-1-propanol. $[\alpha]_D$: −22.1° (c=1.1, CHCl$_3$). By dissolving this product in diethyl ether and passing a hydrogen chloride gas therethrough, 2.13 g of (−)-erythro-2-amino-1-(2-methoxy-5-methylphenyl)-1-propanol hydrochloride was obtained. This salt was recrystallized from isopropanol to obtain 1.65 g of the crystal. $[\alpha]_D$: −22.2° (c=1.0, water). The optical purity of this product as sugar derivative (diastereomer) was 97.8% by high-performance liquid chromatographic analysis.

Reference example 6

31 Grams (0.114 mole) of 2-amino-1-(2,5-diethoxyphenyl)-1-propanone hydrochloride was dissolved in 450 ml of water, and 2.15 g (0.0568 mole) of sodium borohydride was added at 3° to 7° C. After maintaining the temperature for 2 hours with stirring, the reaction solution was acidified with conc. hydrochloric acid and washed with chloroform. The aqueous layer was made alkaline with a 25% aqueous sodium hydroxide solution and extracted with chloroform to obtain 24.1 g of (±)-erythro-2-amino-1-(2,5-diethoxyphenyl)-1-propanol (erythro/threo=93.6/6.4). This product was recrystallized from toluene to obtain 21.0 g of a crystal (erythro/threo=98.4/1.6).

m.p., 108°–109° C.

NMR spectrum (CDCl$_3$): δ(ppm): 0.99 (d 3H), 1.37 (t 6H), 1.4–2.2 (broad 2H), 3.24 (m H), 3.98 (q 4H), 4.72 (d H), 6.74 (2H), 6.96 (H)

Reference example 7

20 Grams (0.0938 mole) of 2-amino-1-(2-ethoxyphenyl)-1-propanone hydrochloride was dissolved in 300 ml of water, and 1.77 g (0.0468 mole) of sodium borohydride was added at 5° to 8° C. After maintaining the temperature for 1 hour with stirring, the reaction solution was allowed to stand overnight at room temperature. Thereafter, the reaction solution was acidified with conc. hydrochloric acid and then made alkaline with a 25% aqueous sodium hydroxide solution. The deposited crystal was collected by filtration, washed with water and dried to obtain 13.40 g of erythro-2-amino-1-(2-ethoxyphenyl)-1-propanol as a crystal (erythro/threo =98.4/1.6). This crystal was recrystallized from toluene to obtain 12.39 g of a crystal (content of the erythro-form, 99% or more).

m.p., 89°–91° C.

NMR spectrum (CDCl$_3$): δ(ppm): 0.99 (d 3H), 1.40 (t 3H), 1.6–2.4 (broad 2H), 3.24 (m H), 3.99 (q 2H), 4.76 (d H), 6.7–7.04 (m 2H), 7.05–7.45 (m 2H)

What is claimed is:

1. A method for producing an optically active alcohol having the formula (III),

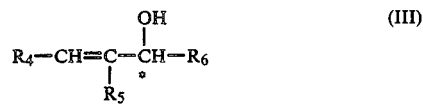

wherein R$_4$ represents cycloalkyl or phenyl which may be substituted with a halogen atom, or haloalkyl, R$_5$ represents 1,2,4-triazol-1-yl, R$_6$ represents tert-butyl and * designates an asymmetric carbon atom, which comprises asymmetrically reducing a ketone having the formula (II),

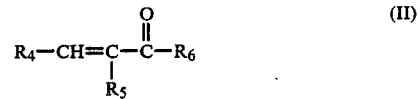

wherein R$_4$, R$_5$, and R$_6$ have the same meanings as above, with an asymmetrically modified borohydride compound obtained by reacting a borohydride with an optically active amino alcohol having the formula (I),

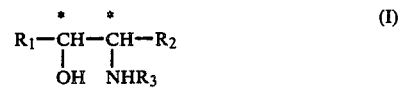

wherein R$_1$ represents phenyl which may be substituted with C$_1$–C$_3$ alkyl or C$_1$–C$_3$ alkoxy, C$_1$–C$_3$ alkyl, or naphthyl, R$_2$ represents phenyl, C$_1$–C$_3$ alkyl or alkoxycarbonyl having 2–7 carbon atoms, R$_3$ represents hydrogen or C$_1$–C$_3$ alkyl and * has the same meaning as above.

2. A method according to claim 1, wherein, in the above formulae (II) and (III), R$_4$ is a C$_6$–C$_{10}$ cycloalkyl or phenyl which may be substituted with halogen, C$_1$–C$_{10}$ haloalkyl or C$_1$–C$_{10}$ alkyl.

3. A method according to claim 1, wherein, in the above formulae (II) and (III), R$_4$ is a 2,4-dichlorophenyl group, R$_5$ is a 1,2,4-triazol-1-yl group and R$_6$ is a tert-butyl group.

4. A method according to claim 1, wherein, in the above formulae (II) and (III), R$_4$ is a 4-chlorophenyl group, $R_5$ is a 1,2,4-triazol-1-yl group and $R_6$ is a tert-butyl group.

5. A method according to claim 1, wherein, in the above formulae (II) and (III), $R_4$ is a cyclohexyl group, $R_5$ is a 1,2,4-triazol-1-yl group and $R_6$ is a tert-butyl group.

6. A method according to claim 1, wherein, in the above formula (I) $R_1$ is phenyl which may be substituted with $C_1$-$C_8$ alkyl or $C_1$-$C_3$ alkoxy, $C_1$-$C_3$ alkyl, or naphthyl and $R_3$ is hydrogen.

7. A method according to claim 1, wherein, in the above formula (I), $R_1$ is phenyl which may be substituted with $C_1$-$C_3$ alkyl or $C_1$-$C_3$ alkoxy or naphthyl, $R_2$ is $C_1$-$C_3$ alkyl, and $R_3$ is hydrogen.

8. A method according to claim 1, wherein, in the above formula (I), $R_1$ is a naphthyl group, $R_2$ is a methyl group and $R_3$ is a hydrogen atom.

9. A method according to claim 1, wherein, in the above formula (I), $R_1$ is a 2,4-dimethoxyphenyl group, $R_2$ is a methyl group and $R_3$ is a hydrogen atom.

10. A method according to claim 1, wherein, in the above formula (I), $R_1$ is a 2,5-diethoxyphenyl group, $R_2$ is a methyl group and $R_3$ is a hydrogen atom.

11. A method according to claim 1, wherein, in the above formula (I), $R_1$ is a 2,5-dimethoxyphenyl group, $R_2$ is a methyl group and $R_3$ is a hydrogen atom.

12. A method according to claim 1, wherein, in the above formula (I), $R_1$ is a 2-methoxyphenyl group, $R_2$ is a methyl group and $R_3$ is a hydrogen atom.

13. A method according to claim 1, wherein, in the above formula (I), $R_1$ is a 2-ethoxyphenyl group, $R_2$ is a methyl group and $R_3$ is a hydrogen atom.

14. A method according to claim 1, wherein, in the above formula (I), $R_1$ is a 2,5-dimethylphenyl group, $R_2$ is a methyl group and $R_3$ is a hydrogen atom.

15. A method according to claim 1, wherein, in the above formula (I), $R_1$ is a phenyl group, $R_2$ is a methyl group and $R_3$ is a hydrogen atom.

16. A method according to claim 1, wherein the borohydride compound is a metal borohydride.

17. A method according to claim 16, wherein the metal borohydride is sodium borohydride, potassium borohydride, lithium borohydride or zinc borohydride.

18. A method according to claim 16, wherein the asymetrically modified borohydride compound is obtained by reacting the metal borohydride with a salt of the optically active amino alcohol with a mineral acid, carboxylic acid or organic sulfonic acid.

19. A method according to claim 16, wherein the molar ratio of the salt of the optically active amino alcohol to the metal borohydride is 1:0.7 to 1:1.3, as converted to boron basis.

20. A method according to claim 1, wherein the borohydride compound is a borane.

21. A method according to claim 20, wherein the molar ratio of the optically active amino alcohol to the borane is 1:0.7 to 1:1.3, as converted to boron basis.

22. A method according to claim 16, wherein the asymmetric reduction is carried out in the presence of an acid.

23. A method according to claim 22, wherein the acid is Lewis acids, organic acids or mineral acids.

* * * * *

UNITED STATES PATENT AND TRADEMARK OFFICE
CERTIFICATE OF CORRECTION

PATENT NO. : 4,760,149

DATED : July 26, 1988

INVENTOR(S) : Yukio YONEYOSHI et al.

It is certified that error appears in the above-identified patent and that said Letters Patent is hereby corrected as shown below:

On the title page, after "[63]" and before "Continuation-in-part" insert --PCT/JP84/00161 filed Apr. 3, 1984.--

On the title page, under [30] Foreign Application Priority Data should read

```
--Apr.  4, 1983    [JP]      Japan ........... 58-59594
  Dec. 12, 1983    [JP]      Japan ........... 58-234859
  Feb. 20, 1984    [JP]      Japan ........... 59-31127--
```

Signed and Sealed this

Tenth Day of July, 1990

*Attest:*

HARRY F. MANBECK, JR.

*Attesting Officer*  *Commissioner of Patents and Trademarks*